(12) United States Patent
Eisermann et al.

(10) Patent No.: US 6,342,055 B1
(45) Date of Patent: Jan. 29, 2002

(54) BONE FIXATION SYSTEM

(75) Inventors: Lukas G. Eisermann, Akron; Randall R. Theken, Barberton, both of OH (US)

(73) Assignee: Theken Surgical LLC, Barberton, OH (US)

( * ) Notice: Subject to any disclaimer, the term of this patent is extended or adjusted under 35 U.S.C. 154(b) by 0 days.

(21) Appl. No.: 09/322,545

(22) Filed: May 28, 1999

Related U.S. Application Data

(60) Provisional application No. 60/131,483, filed on Apr. 29, 1999.

(51) Int. Cl.[7] .............................................. A61B 17/80
(52) U.S. Cl. .......................................... 606/69; 606/60
(58) Field of Search .............................. 606/53, 60, 61, 606/69, 70, 73, 76

(56) References Cited

U.S. PATENT DOCUMENTS

| | | | | |
|---|---|---|---|---|
| 4,512,038 A | * | 4/1985 | Alexander et al. | 623/23.75 |
| 5,634,926 A | * | 6/1997 | Jobe | 606/69 |
| 5,824,088 A | * | 10/1998 | Kirsch | 623/16 |
| 5,876,402 A | * | 3/1999 | Errico et al. | 606/61 |
| 6,017,345 A | * | 1/2000 | Richelsoph | 606/70 |
| 6,139,550 A | * | 10/2000 | Michelson | 606/69 |
| 6,193,721 B1 | * | 2/2001 | Michelson | 606/70 |

\* cited by examiner

*Primary Examiner*—Gene Mancene
*Assistant Examiner*—Michael B. Priddy
(74) *Attorney, Agent, or Firm*—Frost Brown Todd LLC; Robert H. Eichenberger; Charles Lee Thomason

(57) ABSTRACT

A novel apparatus for securing the head of a screw in a bone plate is disclosed in which bone fasteners or screws snap-fit into an undercut of fastener receiving openings of the bone plate. The bone fasteners or screws are designed such that they may be removed or repositioned from the snap-fit undercuts with the aid of a driver instrument. An embodiment is also disclosed in which a fusion cage is utilized in connection with bone plate and fasteners.

24 Claims, 11 Drawing Sheets

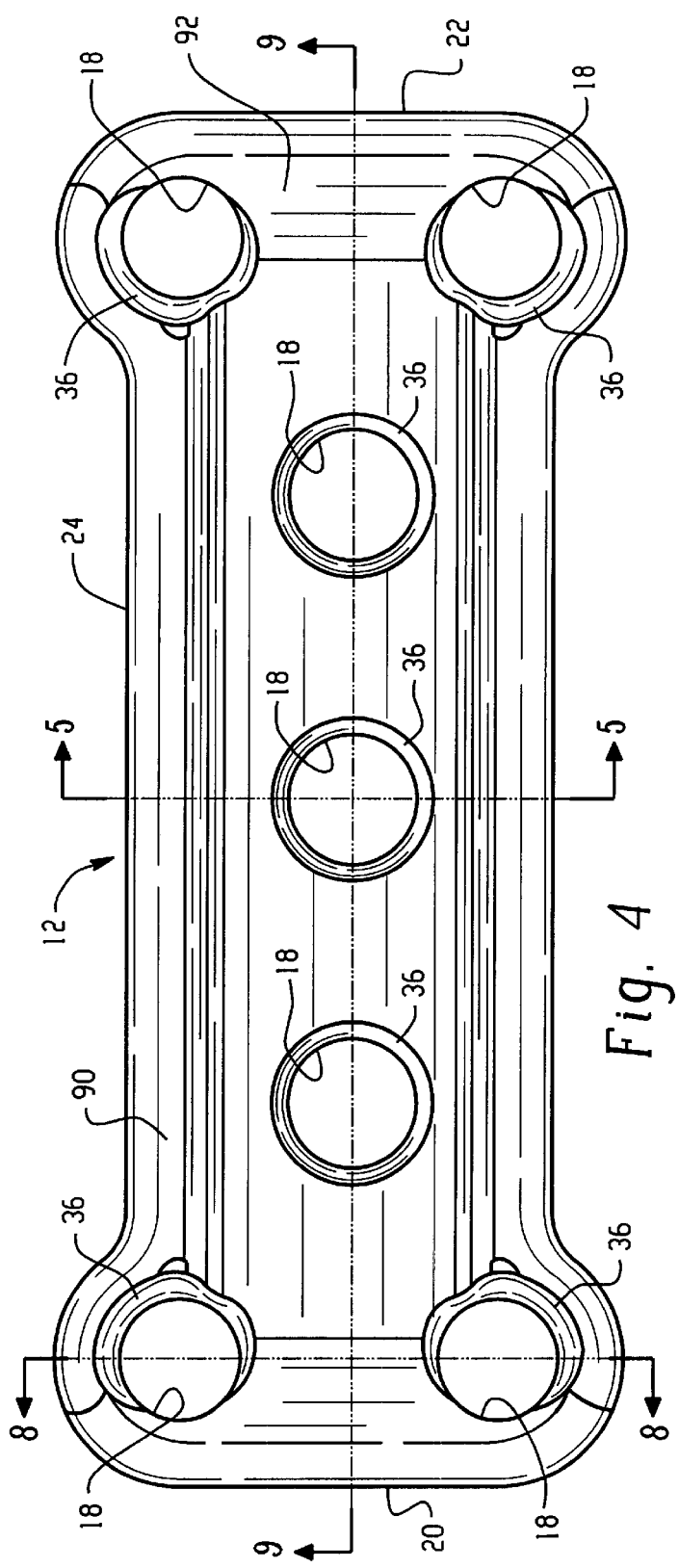
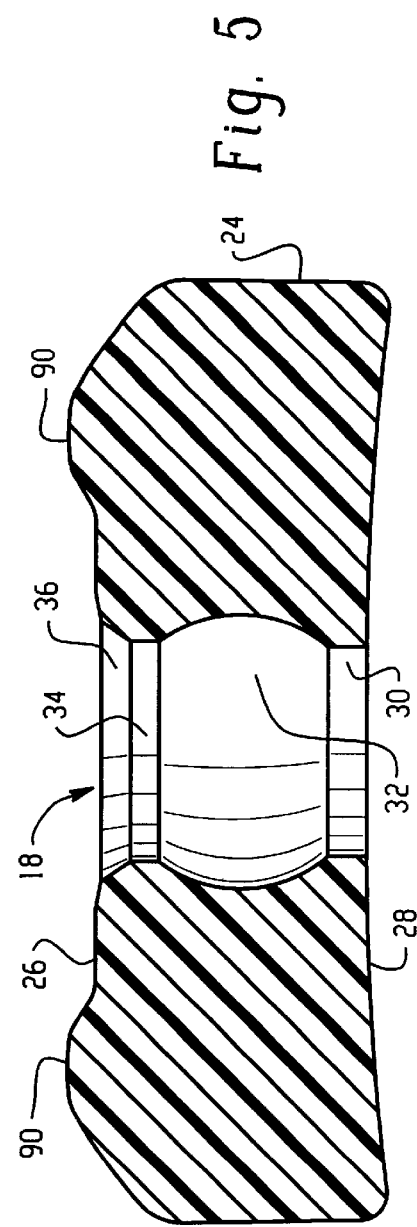
Fig. 4
Fig. 5

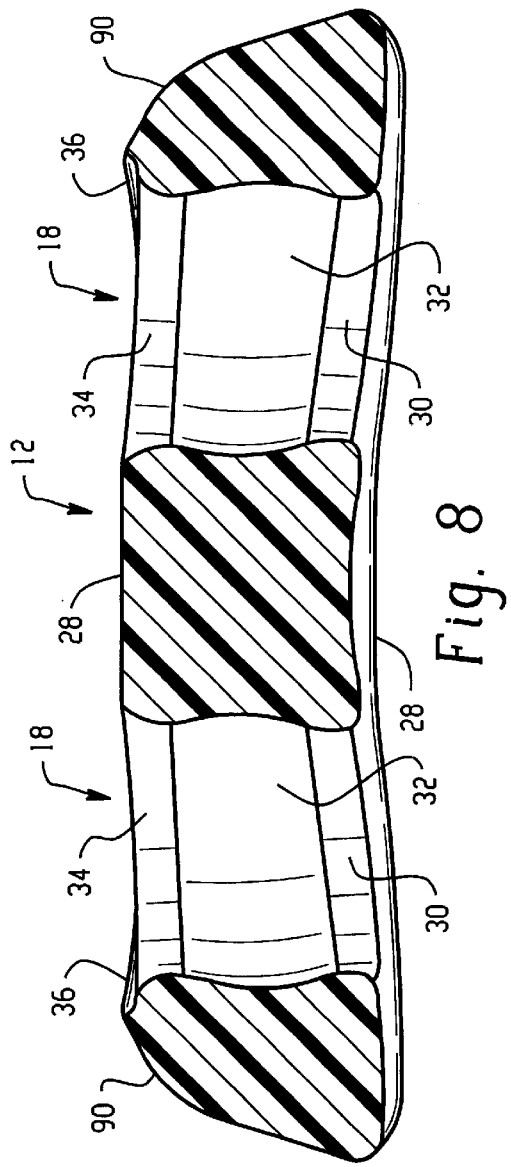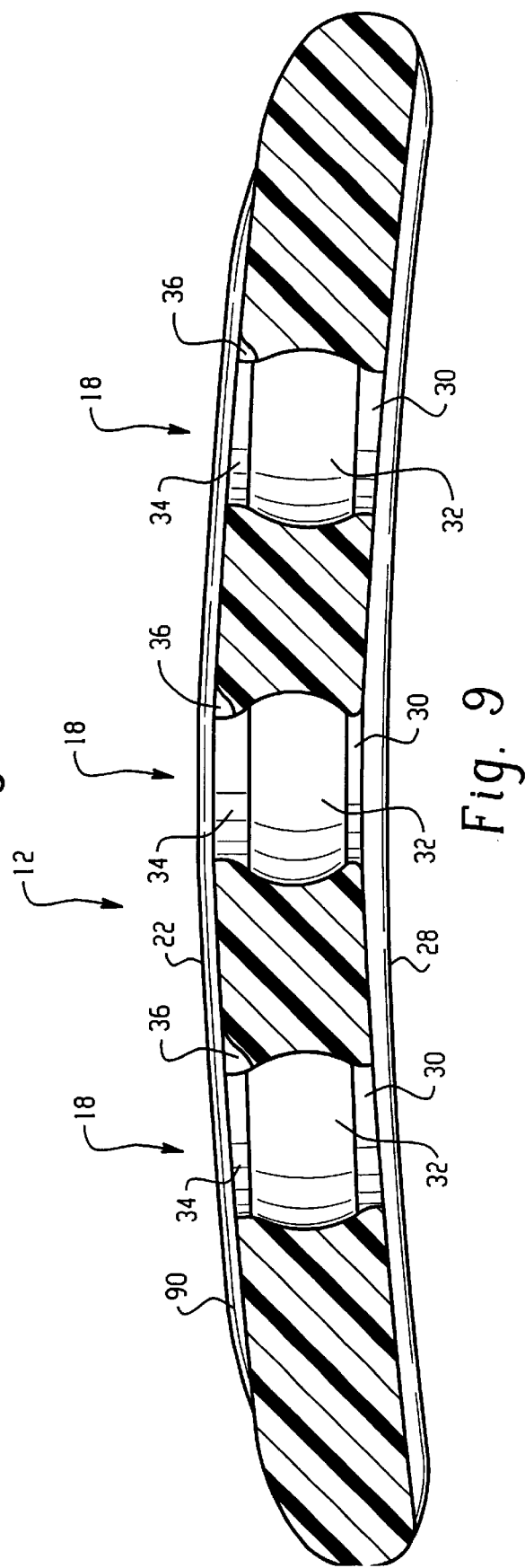

BONE FIXATION SYSTEM

This patent application claims the benefit of U.S. Provisional Application No. 60/131,483, filed Apr. 29, 1999.

FIELD OF THE INVENTION

The present invention generally relates to a system for fixing the relative positions of one or more bone segments by the use of bone plates and screws, and more specifically to such a system which prevents screw back-out without resort to secondary locking devices.

BACKGROUND OF THE INVENTION

The use of bone plate and bone screw fixation systems for treating injuries to bones is well established. In most instances, a bone plate is engaged to a bone with the plate over and surrounding the bone injury area. The bone plate is affixed to the bone by bone screws or other similar fasteners inserted through holes in the bone plate and into the bone itself. The screws are tightened so that the bone plate holds the bone to be treated in place in order to insure proper healing. Early fixation devices tended to be applicable only to long bone injuries with some limited uses for lower lumbar spinal injuries and disorders. The use of plate/screw fixation systems expanded, however, to include uses for more spinal injuries and fusion of vertebrae including fixation devices for treating cervical vertebrae injuries. While these systems are applicable to spinal injuries, they tend to encounter a variety of problems which lead to less than optimal results. These problems include, amongst others, "backout."

Backout is the exhibited tendency of bone screws, which affix the bone plate to the bone(s), to loosen with respect to both the plate and bone resulting in poor fixation, fusion and ultimately, healing. Essentially, this loosening of the bone screw causes the screw to work itself out of the bone into which it is implanted. This results in the bone plate being poorly fixed in place thus becoming devoid of its fixation capabilities. Usually, backout is caused by the stress of bodily movement. While such loosening can be benign if limited in scope, it more often leads to complications such as complete failure of the fixation device or incomplete bone fusion. Backout is particularly prevalent in areas of high bodily stress, such as the spine.

To alleviate backout and its associated problems, current systems utilize secondary locking screws, locking collars or other secondary locking devices that hold the bone screws in place after deployment within the bone. In most systems, the bone screw is affixed into the bone through an opening in a bone plate. A locking device is then inserted into the bone screw. The locking device engages the head of the bone screw and is tightened which results in the bone screw being fixed in place within the bone, thus preventing backout.

While a locking screw or collar can alleviate backout, successful use of such locking device systems in the anterior cervical spine is particularly difficult because limited operating space is available due to anatomic constraints. Systems using multiple types of screws or collars to hold the bone screw in place are difficult to deploy within the confines of the small operating area of the cervical spine. Furthermore, due to the small operating area, the surgeon implanting the device has great difficulty determining if the device is properly deployed. Any instrumentation implanted in the region must be minimally intrusive, yet have adequate strength to withstand the biomechanical loads to which it will be subjected. Thus, while current systems can help reduce instances of backout, their complex nature makes proper deployment very difficult and increases the chance of surgical error.

Current treatment methods also call for instrumentation which is able to provide both rigid fixation and semi-rigid, or "dynamized," fixation that allows the implant to accommodate graft settling. Backout, however, limits the use of such dynamized fixation because the locking devices do not accommodate for graft settling.

Prior art systems, while addressing some of the requirements for successful anterior cervical spinal instrumentation, share several other common deficiencies. Early systems were typically produced using stainless steel components. These stainless steel components interfered with magnetic resonance imaging (MRI) equipment, resulting in poor-quality postoperative imaging of the fixation system. Current systems have changed materials to commercially pure titanium and titanium alloy in order to reduce the MRI noise. However, some noise artifacts remain. Also, the anterior-posterior image obtained via X-ray based methods cannot be used to evaluate graft healing progress, since metallic implant components block X-rays.

Thus, a need exists for an instrumentation system which decreases the surgical complexity of anterior cervical instrumentation and eliminates backout while providing enhanced postoperative imaging possibilities and structural integrity. Reducing the complexity of the instrumentation decreases the chance for surgical error, reduces the time required to implant a fixation device, and reduces the cost of the surgery. Providing enhanced postoperative imaging capability increases the surgeon's ability to evaluate the healing progress. Accordingly, a system allowing for easy deployment while eliminating backout, retaining structural integrity and improving imaging capabilities is needed in the art.

SUMMARY OF THE INVENTION

The bone fixation system of the present invention addresses and overcomes problems found in the prior art. In accordance with one aspect of the invention, a system for anterior fixation of bones of the cervical spine is provided which includes an elongated bone plate sufficient in length to span at least two vertebrae with the plate including one or more holes shaped to accept the head of a mating fastener such as a bone screw.

To eliminate backout, one or more of the holes in the device are formed by creating an undercut within at least a portion of the hole. Preferably, the undercut has a spherical concavity configuration, but other geometries can also perform the required functions of the device and eliminate back-out. Bone screws are provided with a head portion whose geometrical configuration allows for engaging of the head portion with the undercut. As the screw is driven through the plate and into the bone, the head portion of the screw will engage the undercut ultimately "snapping" into the undercut which then securely retains the screw and provides sufficient force to prevent postoperative backout.

In accordance with another aspect of the present invention, in the event that a screw does need to be removed from the bone and/or plate or be repositioned, a driving instrument is provided that can be used to disengage the snap-fit interface while securely retaining the screw. The driving instrument consists of a cannulated shaft with at least one prong or flat to engage the screw head, and a draw rod that inserts through the cannulated shaft to thread into the screw head.

To remove a screw, the device is held in place, either by other screws that have already been placed, or by holding the bone plate down by some other instrument. The screw is then rotated to disengage the thread from the bone. As the screw is rotated, the surgeon pulls the screw out of the snap-fit undercut to prevent thread stripping. Since the screw is securely gripped by the draw-rod driving instrument, the surgeon is able to apply sufficient tensile force to pull the head portion of the screw out of the undercut.

Another aspect of the present invention is that the bone plate of the invention is made from a composite material with radiolucent properties that allows for clear, undistorted postoperative MRI images to be produced. The composite bone plates do not contribute noise artifacts to the MRI image, and are also invisible to the imaging equipment. The bone screws of the present invention are made from titanium or a titanium alloy to act as clearly visible marker posts which provide the surgeon with postoperative position data.

In yet another aspect of the present invention, stress-controlling ridges are included on one surface of the bone plate to increase the fatigue life of the device. Without stress-controlling ridges present on the tensile surface of the plate, the highest stress concentrations due to the expected loading conditions occur in the vicinity of the undercut screw holes. This is a result of stress concentrations that can be approximated using fracture mechanics theories.

The stress-controlling ridges are located at a distance further from the neutral axis than the most extreme plane of the undercut screw holes. As a result, the bending stress on the plane containing the undercut screw holes is not the highest stress in the bone plate. Instead, the stress-controlling ridges are the highest stress regions of the bone plate. The ridges are produced so that they are continuous and unnotched, thus providing significantly improved fatigue performance compared to devices that do not have such ridges.

The present invention also provides an embodiment in which a fusion cage is incorporated into the bone plate. During deployment, the fusion cage, which is packed with a tissue graft, is placed in the area between two vertebrae. The bone plate is then affixed to the vertebrae in a manner consistent with other embodiments of the invention. Thus, this embodiment allows for increased bone graft and fusion to occur while retaining the aforementioned properties of the other embodiment of the present invention.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein:

FIG. 4 is a detail view of the bone plate, seen facing the anterior surface.

FIG. 5 is a cross-sectional view of the undercut fastener receiving opening and stress controlling ridges according to an embodiment of the present invention, taken along line 5—5 of FIG. 4.

FIG. 8 is a cross-sectional view of the plate, taken along line 8—8 of FIG. 4.

FIG. 9 is a cross-sectional view of the plate, taken along line 9—9 of FIG. 4.

DETAILED DESCRIPTION OF THE PREFERRED EMBODIMENT

Figure 1:
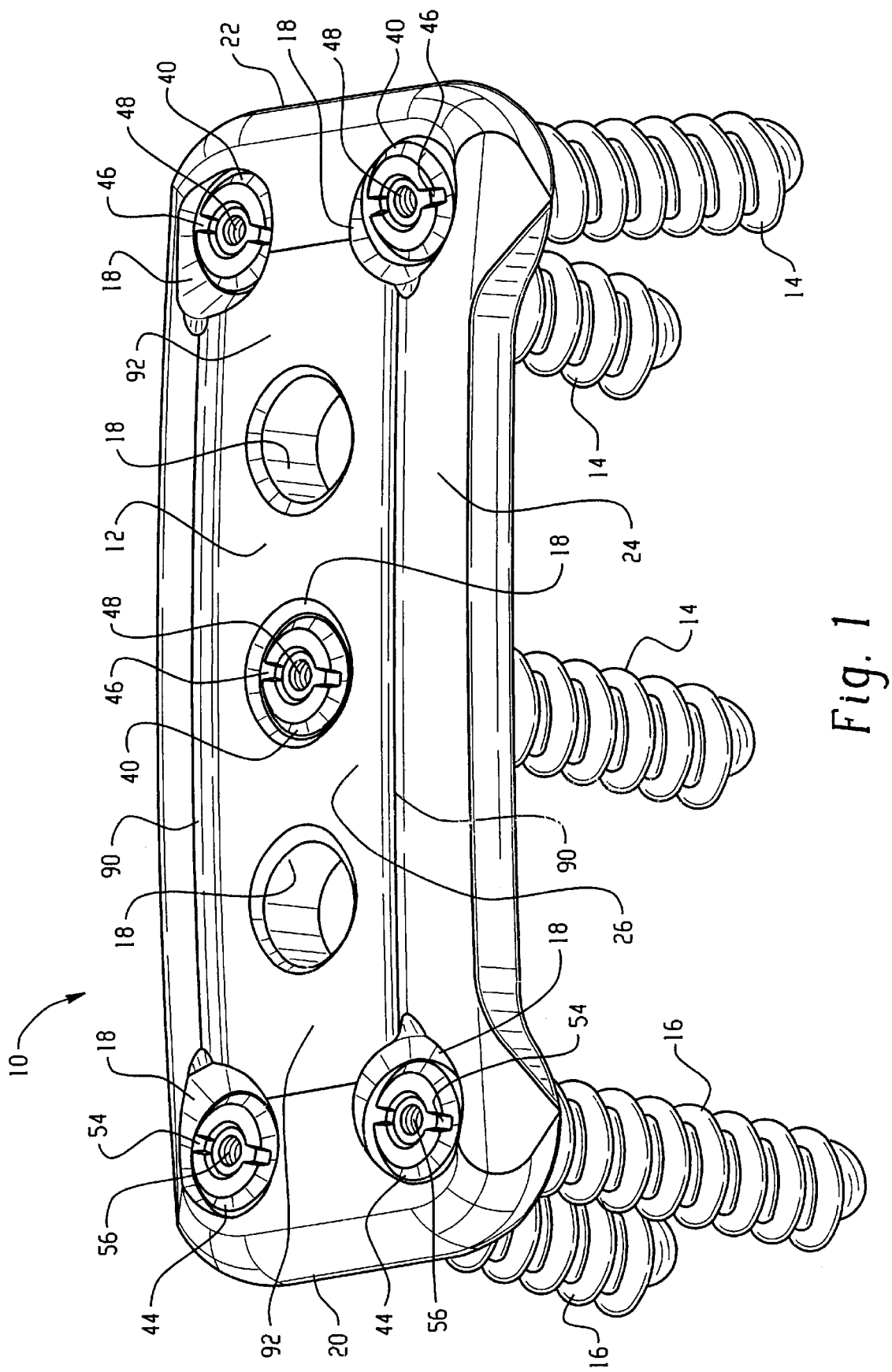
FIG. 1 is a view of the of the fixation system according to an embodiment of the present invention.
Figure 3:
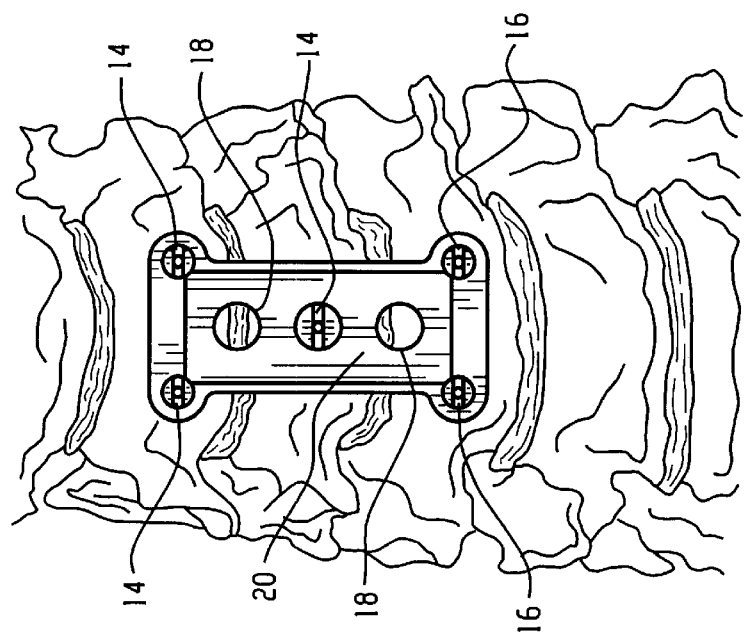
FIG. 3 is a view of the fixation system according to an embodiment of the present invention, as installed, as viewed facing the anterior surface.

For the purposes of understanding the principles of the invention, references will now be made to the embodiments illustrated in the drawings. It should be appreciated, however, that the present invention is also contemplated for use in connection with fixation systems other than anterior cervical fixation. In this regard, the present invention finds application in the treatment of bone structures in other regions of the spine as well as bone structures located in regions outside the spine.

Figure 2B:
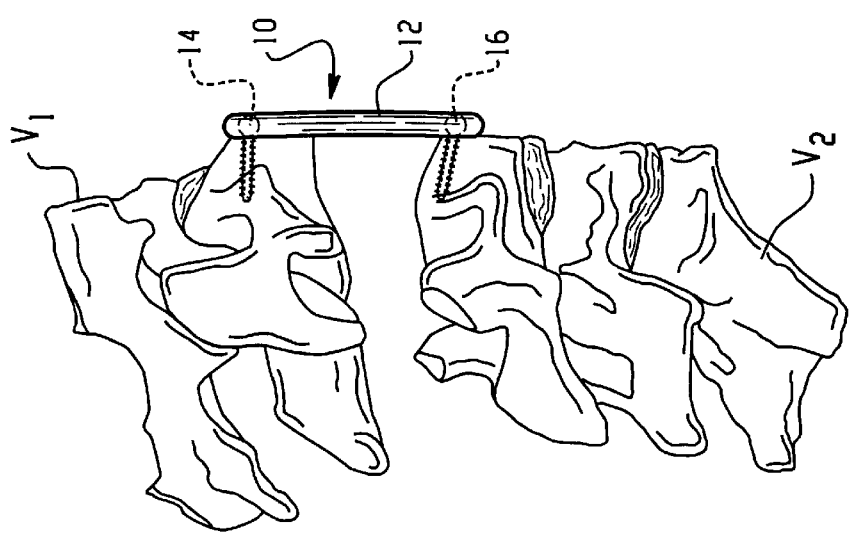
FIGS. 2a and 2b are cross-sectional views of a fixation system installed according to a preferred embodiment of the present invention.
Figure 2A:
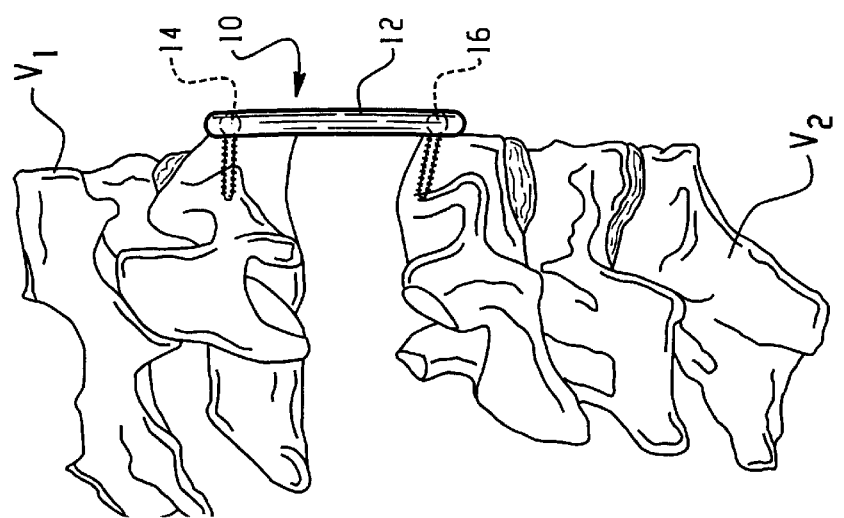
Figure 6:
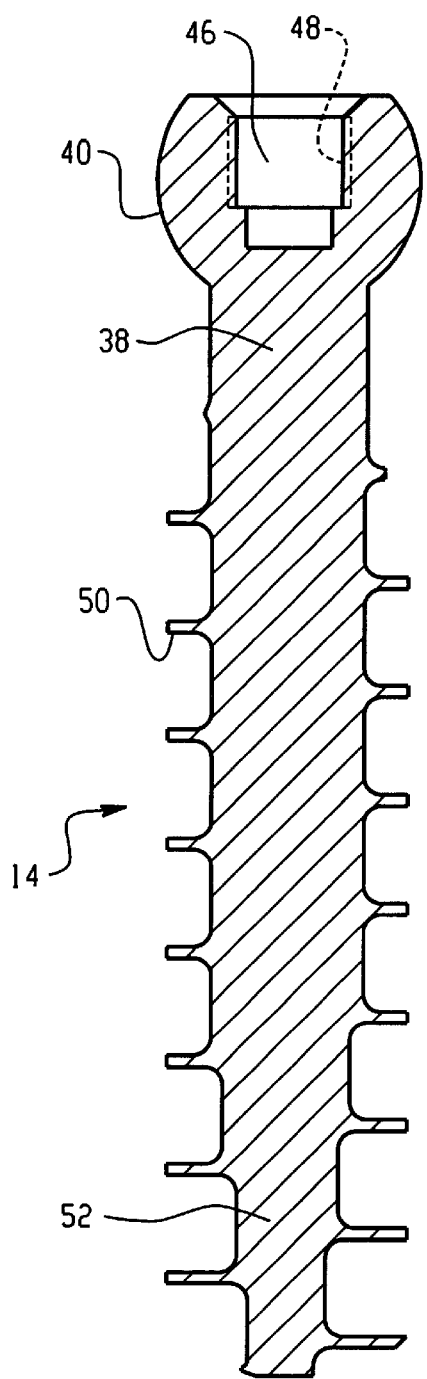
FIG. 6 is a cross-sectional view of a semi-rigid fixation bone screw according to an embodiment of the present invention.
Figure 7:
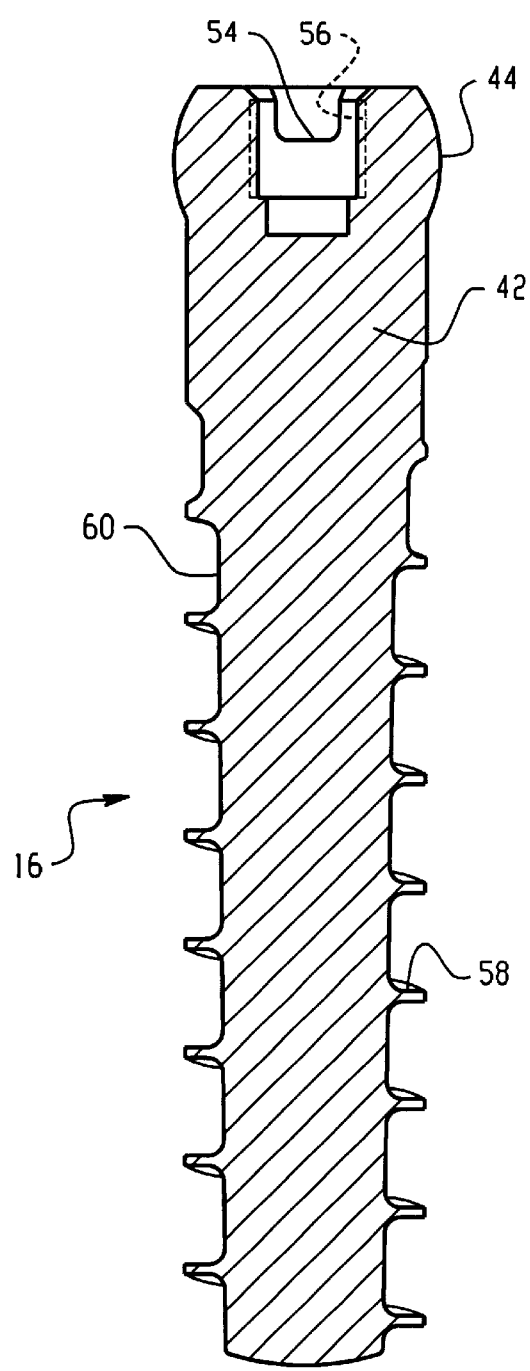
FIG. 7 is a cross-sectional view of a rigid fixation bone screw according to an embodiment of the present invention.

Referring now to the drawings, FIG. 1 shows an isometric view of a bone fixation system 10 according to an embodiment of the present invention. Bone fixation system 10 is generally comprised of a bone plate 12 a plurality of fasteners such as semi-rigid screws 14 and/or a plurality of rigid screws 16. Fully assembled, semi-rigid screws 14 and/or rigid screws 16 are inserted through fastener receiving openings 18 formed in the bone plate 12 and driven into a bone structure. FIGS. 2a and 2b illustrate the bone fixation system 10 as attached to vertebral bodies $V_1$ and $V_2$. In the embodiment of the invention described below, bone fixation system 10 is configured for fixation to the human cervical spine by means of an anterior approach but it would be known to one skilled in the art that a present invention is readily adaptable to other bone configurations including other spinal locations.

With reference to FIGS. 1, 2a, 2b, 8 and 9, the bone plate 10 will be described in detail. The bone plate 10 is generally comprised of two end portions 20, 22, a bridge portion 24, an anterior surface 26, a posterior surface 28, and one or more fastener receiving openings 18. Bone plate 12 has a length sufficient to span at least the space between two vertebrae. It should be appreciated, however, that applications for the present invention are considered where the bone plate 12 does not have such length limitation. It should also be appreciated that the length required for bone plate 12 in any particular installation is dependent upon the condition to be corrected which can include any number of vertebrae to be held in a desired spatial relationship relative to each other by the bone plate 12.

Preferably, the bone plate 12 is made from radiolucent composite polymer material, but it is contemplated that one of skill in the art would readily appreciate that the bone plate 12 may be made from a radiopaque material. Radiolucent composite materials that can be utilized include carbon-fiber reinforced polymer composites from the polyaryletherketone family (i.e.—polyetheretherketone (PEEK), polyetherketoneetherketoneketone (PEKEKK), etc.). In a preferred embodiment, the composite polymer bone plate material is composed of approximately 70% polyetheretherketone and 30% chopped carbon fiber with the chopped carbon fiber oriented randomly in order to obtain minimal anisotropic behavior.

Typically, the polymer composite can be processed to form the bone plate 12 by injection molding the composite into raw material blocks which are then machined into finished parts, such as bone plates. If desired, finished parts may be further processed by bending the parts into other shapes. Since the composite base resin is thermoplastic, parts made from the base resin can be easily deformed when raised above the resin's transition temperature. It is further contemplated that parts may be molded to a near-finished shape in order to reduce and possibly eliminate the required machining.

The bone plate 12 preferably has a stock width, taken along line 8—8 of FIG. 4, of approximately 18.75 mm with a stock length that varies from 20.0 mm overall to 94.0 mm overall, in a variety of increments. The incremental stock lengths currently available are: 20, 22, 24, 26, 28, 30, 32, 34, 36, 39, 42, 45, 48, 51, 54, 57, 60, 63, 67, 71, 75, 78, 82, 86, 90, and 94 mm, respectively. The lengths represent off-the-shelf stock lengths and do not limit the length of the bone plate 12 in any way. It is contemplated that longer or shorter plates can be readily used as patient need warrants.

The bone plate 12 has radii of curvature in the longitudinal direction for both the anterior and posterior sides of the bone plate 12 as well as having curvature in the transverse direction. The transverse direction radius of curvature is typically only in the posterior surface, but it can be optionally placed in the anterior surface is so desired. The stock radii of curvature in the longitudinal direction are approximately 147 mm, 197 mm, and 247 mm, respectively. The radius of curvature in the transverse direction is about 40.6 mm. The bone plate 12 may be optionally contoured through heating and bending to make nearly any form desired. Thus, it should be readily understood that a bone plate can be manufactured having more than one radius of curvature or other bend, etc. Finally, one of skill in the art would readily apprise that stock width, length and radius of curvature are based on average anatomic values with a wide range of dimensions and radii being combinable to fit a bone plate 12 for patient-specific anterior cervical vertebrae fixation, let alone fixation of other bone structures.

The fasteners 14, 16 can be produced from radiopaque material, such as commercially pure titanium or titanium alloy. It should be readily appreciated that other combinations of materials also may be used to produce the device, including radiolucent materials such as carbon fiber composites.

End portions 20, 22 of bone plate 10 include a pair of openings 18 which are dimensioned to receive a fastener namely, semi-rigid screw 14 or rigid screw 16. Each fastener receiving opening 18 can be generally circular and have a smaller hole section 30, an undercut 32, a larger hole section 34, and a lead-in chamfer 36. The lead-in chamfer 36 and larger hole section 34 are dimensioned to receive a head portion of either semi-rigid screw 14 or rigid screw 16 by means of snap-fitting therein. The undercut 32, which is preferably spherically concave in configuration, is dimensioned to accommodate and retain the head portion of semi-rigid screw 14 or rigid screw 16. It should be noted that the above described method is only one means of achieving the snap-fit connection. The undercut 32 may alternately be located on the head of the fastener. The undercut 32 can also have virtually any geometrical configuration, including, but not limited to, rectangular, octagonal, hexagonal, triangular, circular, cylindrical, elliptical or any other polygonal. Also, the fastener receiving openings 18 in the bone plate 12 could have mating protrusions, rather than undercuts. Multiple undercuts or protrusions may also be provided in either or both the fastener or the plate.

As can be best seen in FIGS. 5 and 8, smaller hole section 30 is dimensioned to have a diameter greater than semi-rigid screw shank 38 such that semi-rigid screw 14 rotates after a head portion 40 of semi-rigid screw 14 is received and retained by spherical concave undercut 32. Preferably, smaller hole section 30 is dimensioned to have diameter approximately equal to diameter of a rigid screw shank 42 such that rigid screw 16 cannot demonstrate appreciable movement when a head portion 44 of rigid screw 16 is received and retained by spherical concave undercut 32. Smaller hole section 30 is dimensioned such that head portion 40 or head portion 44 is prevented from passing through.

While the undercut 32 is preferably spherically concave, any number of configurations can be used, including, but not limited to, square, triangular, or irregular. The undercut 32 simply should have at least a rim portion having a diameter smaller than that of the head portion of the screw such that the head portion elastically deforms when initially engaging the undercut 32 and then snaps into place so that it is held captive within the undercut 32.

Producing the device from the above listed materials and in the aforementioned manner allows the tolerances of the components to be such that the head portion 40, 44 of a screw 14, 16 snaps into an undercut portion 32 of the fastener receiving openings 18 of the bone plate 12 with an amount of force appropriate for the surgical arena. In other words, the force required to engage the snap fit is large enough that the screw head is securely held, but not so large that there is danger of the bone screw stripping the thread in the bone.

Referring to FIGS. 3–7, 9 and 10, a semi-rigid screw 14 is generally comprised of a head portion 40, a shank 38, a slot 46, an internal thread 48, an external thread 50 and a lead-in minor root taper 52. Head portion 40 is generally spherical. Spherical diameter of head portion 40 is generally equal to spherical diameter of spherical concave undercut 32. Shank portion 38 has a diameter that is smaller than diameter of smaller hole section 30. External thread 50 has a diameter that is smaller than diameter of smaller hole section 30. If so desired, lead-in minor root taper 52 may be formed at end of external thread 50. Slot portion 46 is dimensioned to receive nubs of a driver housing. Internal thread portion 48 mates with an external thread portion of a draw rod.

Rigid screw 16 is comprised of a head portion 44, a shank 42, a slot 54, an internal thread 56, an external thread 58 and a washout minor root taper 60. Head portion 44 is generally spherical. Spherical diameter of head portion 44 is generally equal to the spherical diameter of spherical concave undercut 32. Shank portion 42 has a diameter that is generally equal to diameter of smaller hole section 30. External thread 58 has a diameter that is smaller than diameter of smaller hole section 30. Washout minor root taper 60 may be formed at end of external thread 58. Slot portion 54 is dimensioned to receive nubs of a driver housing. Internal thread portion 56 can mate with an external thread portion of a draw rod.

For both semi-rigid screw 14 and rigid screw 16, a cancellous thread is preferred, but not required. A cancellous thread is deeply cut with a large pitch in order to allow extra purchase or anchorage in bone structures of poor quality.

Figure 10:
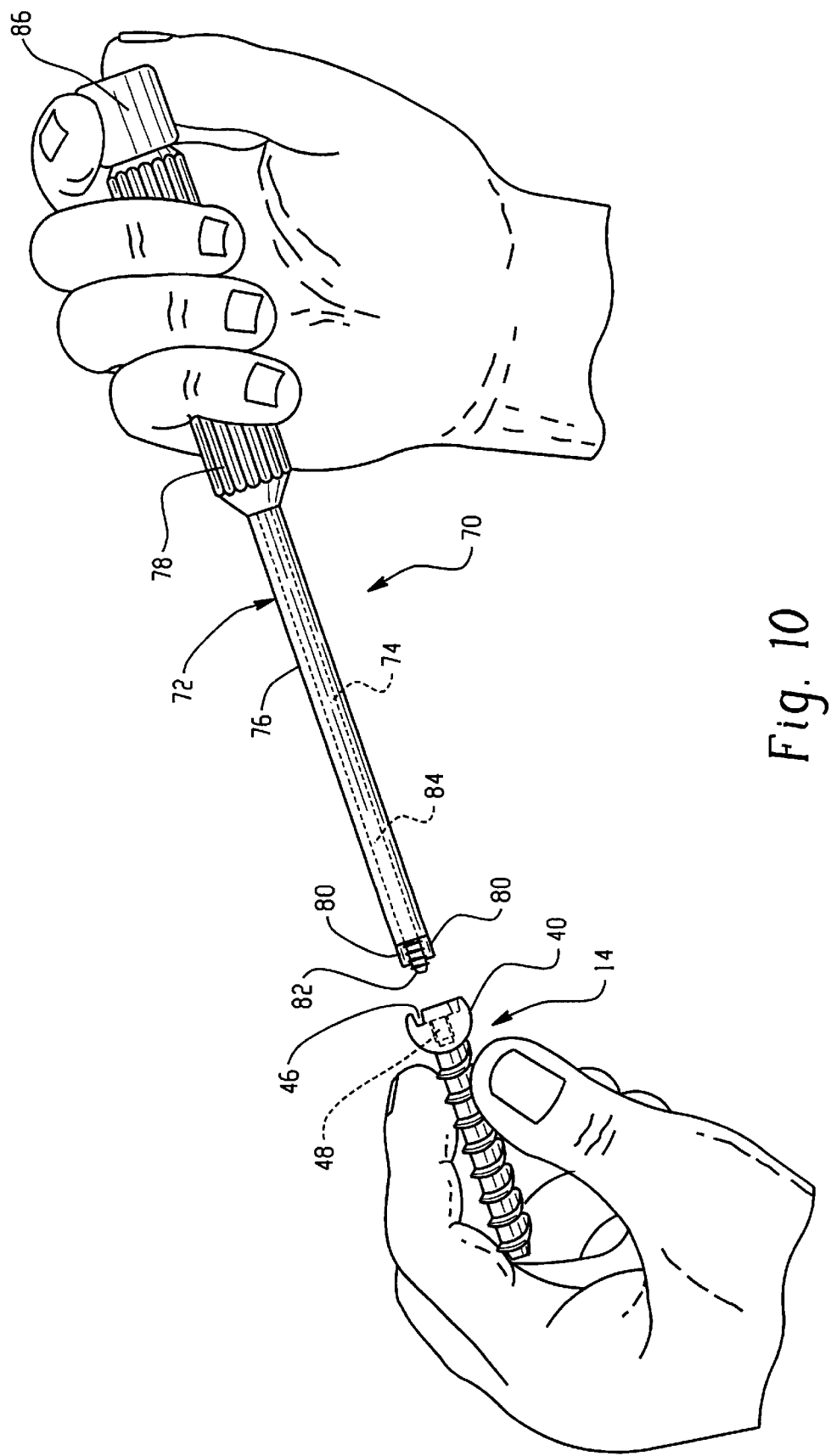
FIG. 10 is a perspective of the draw rod of the driving instrument of the present invention with a bone screw being loaded.
Figure 11:
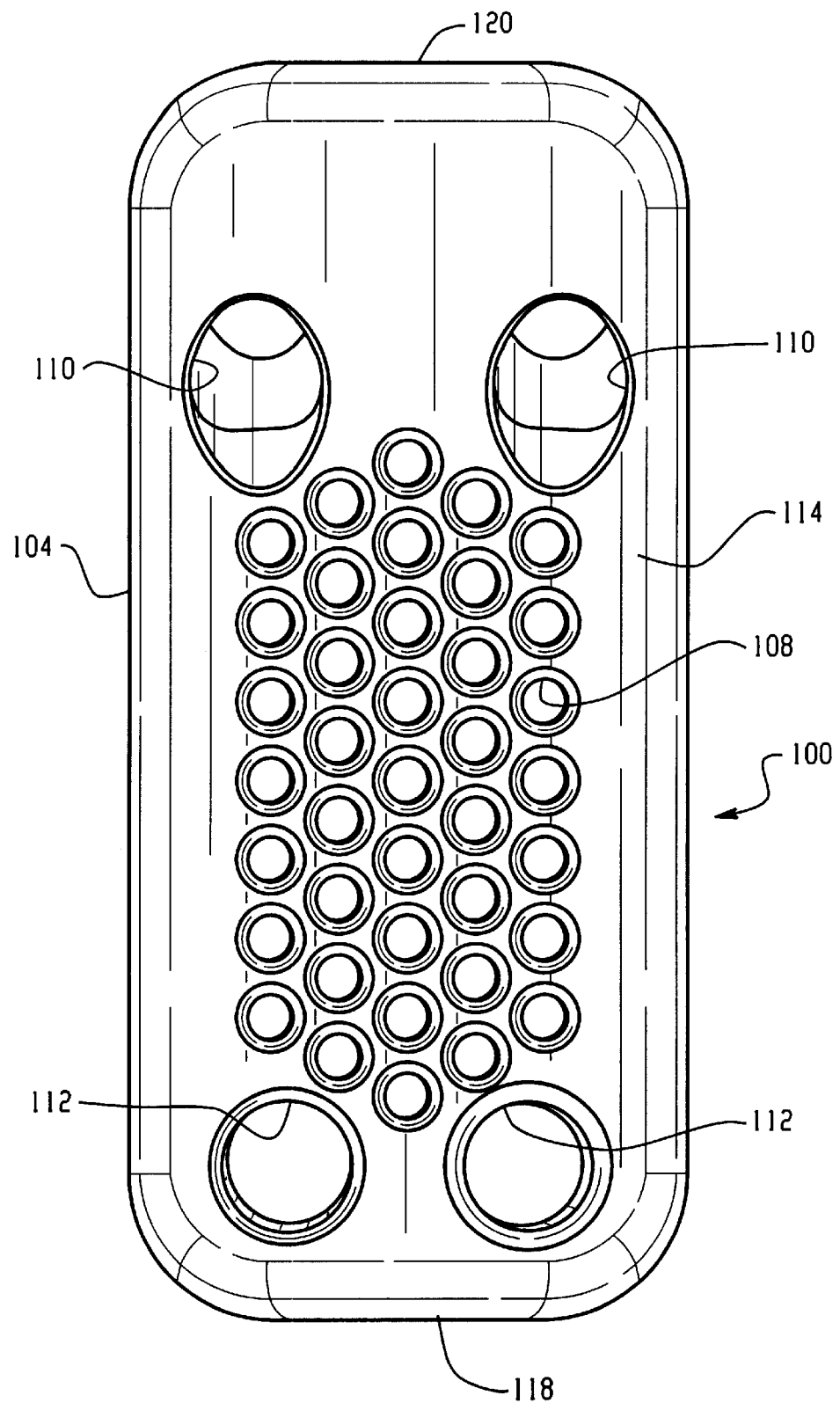
FIG. 11 is a view of the fixation system with fusion cage according to an embodiment of the present invention, as viewed facing the anterior surface.
Figure 12:
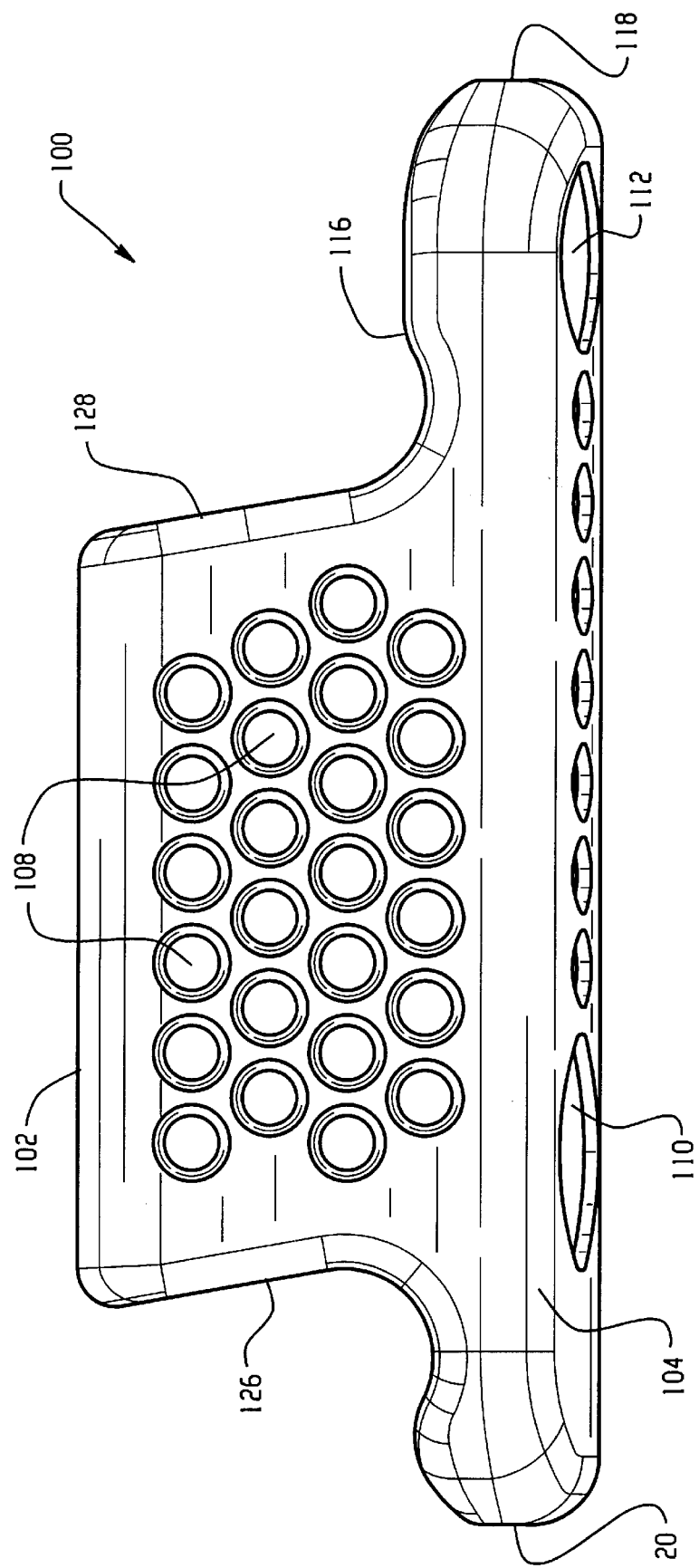
FIG. 12 is a side view of the fixation system having a fusion cage of the present invention.
Figure 13:
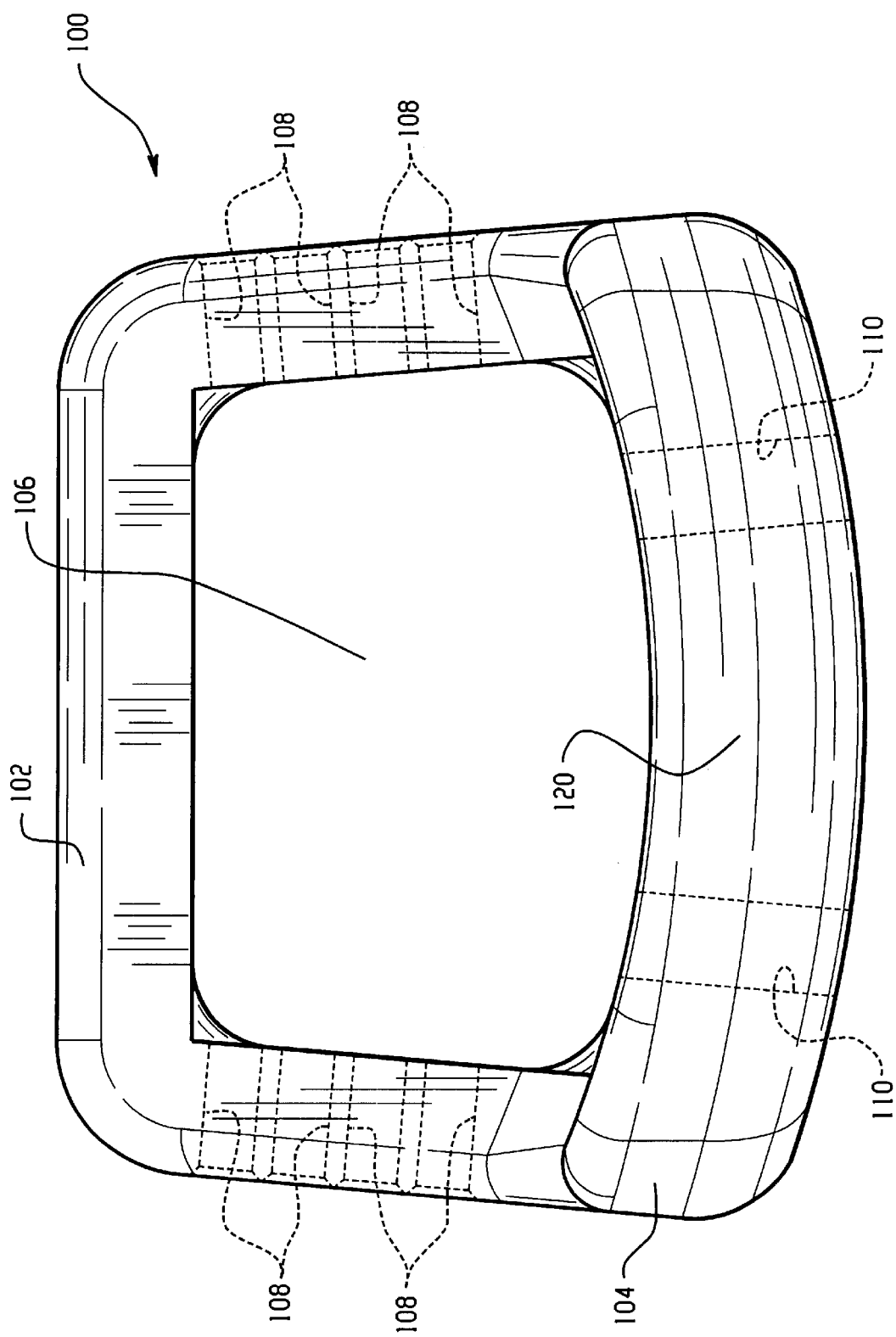
FIG. 13 is an axial view of the fixation system having a fusion cage of the present invention.
Figure 14:
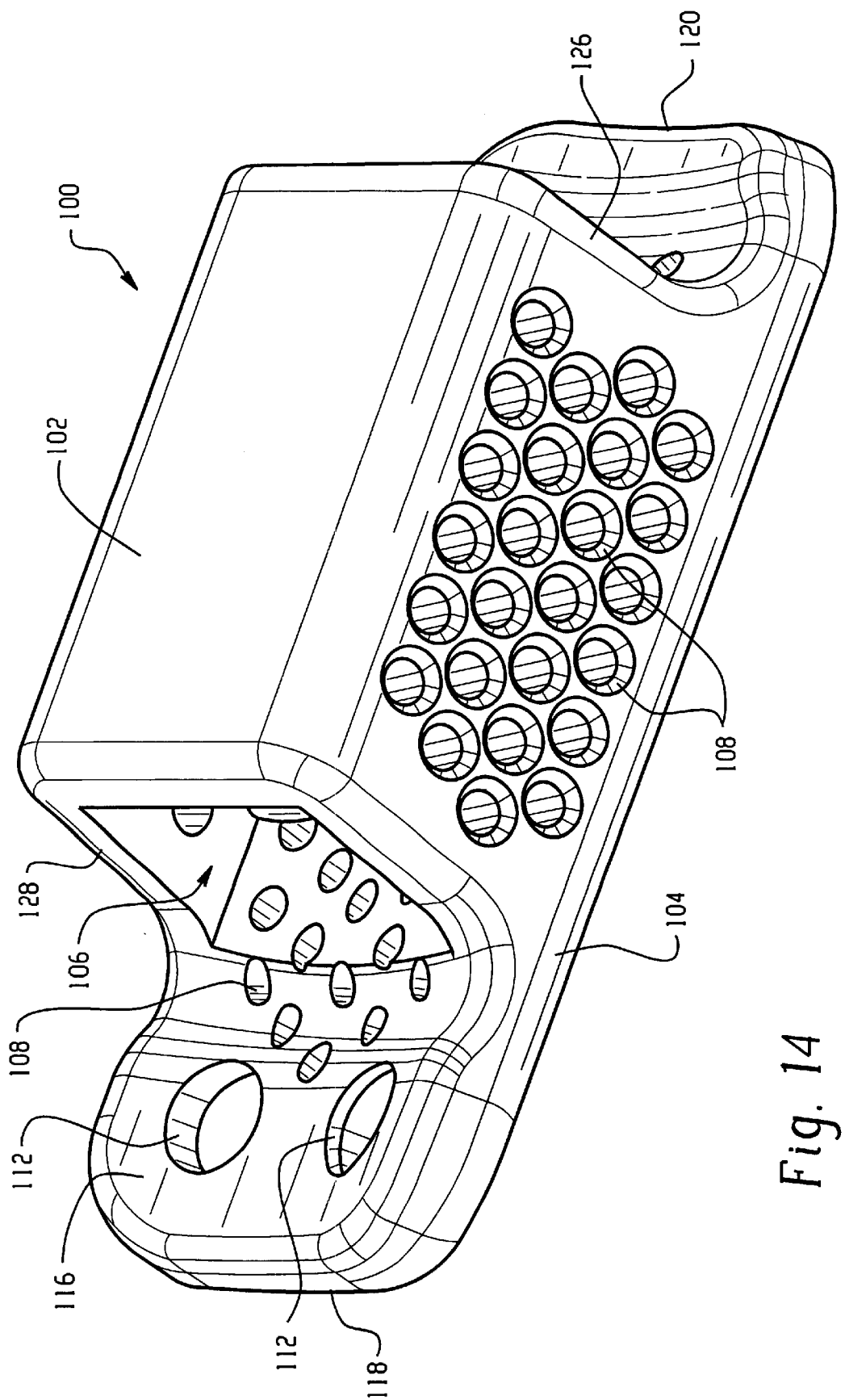
FIG. 14 is a posterior, isometric view of the fixation system having a fusion cage of the present invention.
Figure 15:
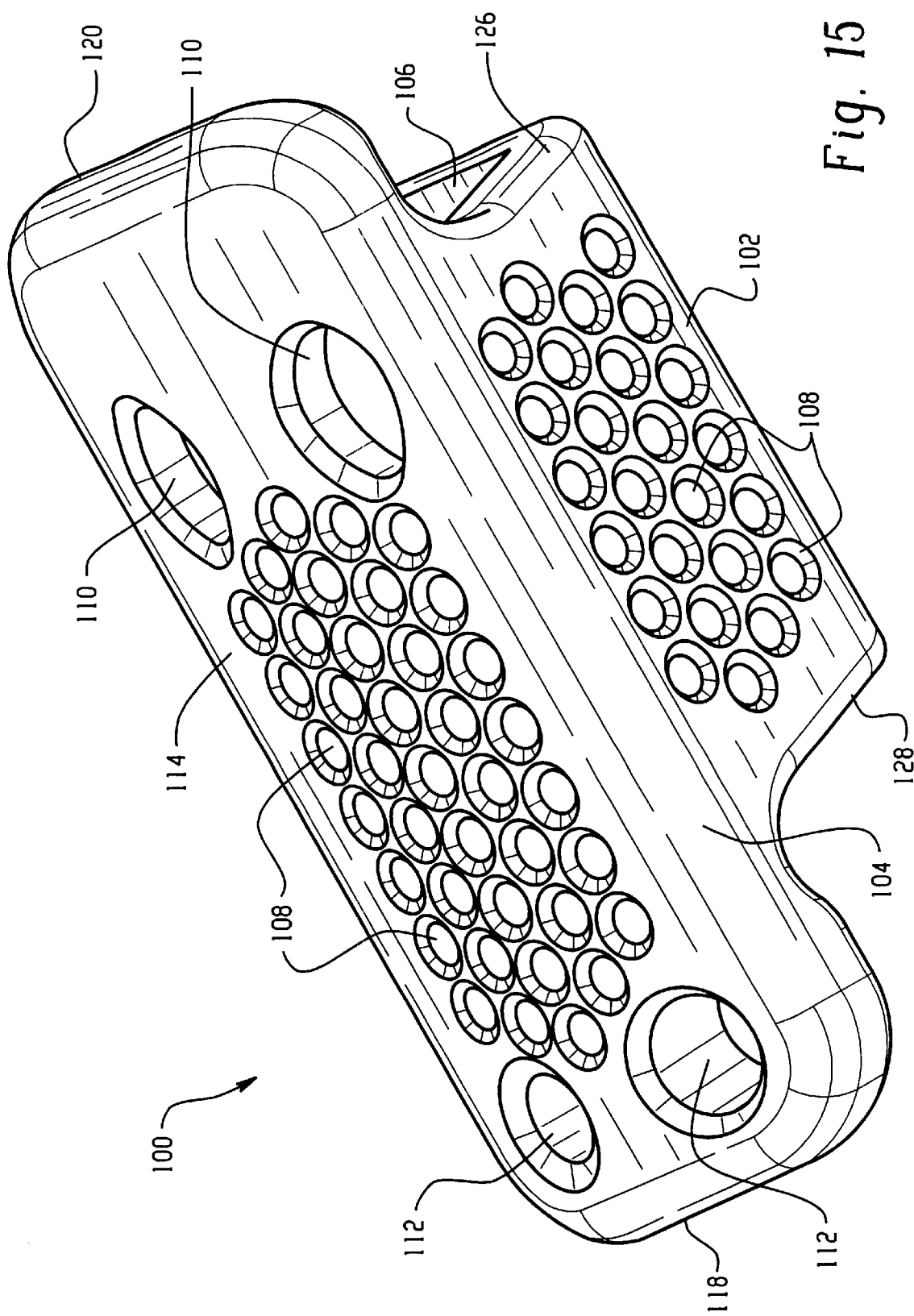
FIG. 15 is an anterior, isometric view of the fixation system having a fusion cage of the present invention.

FIG. 10 generally illustrates a fastener driver 70 generally comprising driver housing 72 and draw rod 74. Driver housing 72 has a cannulated shaft 76, driver housing handle 78 and nubs 80 while draw rod 74 has external thread 82, draw rod shaft 84 and draw rod handle 86. Nubs 80 are dimensioned to be received into slot portion 46 of semi-rigid screw 14 and into slot portion 54 of rigid screw 16. Cannulated shaft 76 is dimensioned to receive draw rod shaft 84. An end of draw rod shaft has an externally threaded portion 82 that mates with internal thread 48 of semi-rigid screws 14 or internal thread 56 of rigid screws 16.

The driver 70 works by inserting draw rod shaft 84 through cannulated shaft 76. Nubs 80 are received by slot 46 or slot 54. Handle 86 is rotated to engage external thread 82 with internal threads 48 or internal threads 56. Engaging of external thread 82 causes screw 14 or screw 16 to be pulled snugly against driver housing 72. Draw rod shaft 84 and cannulated shaft 76 are dimensioned such that tension is generated on the draw rod 74 to hold the screw 14 or the screw 16 firmly in place.

The fixation system 10 is installed by placing plate 12 of appropriate length, across the bone elements to be fixed. Posterior surface 28 contacts the bone elements. Anterior surface 26 faces surgeon. A hole is drilled relatively concentric to one of the fastener receiving openings 18 formed in plate 12. Semi-rigid screw 14 or rigid screw 16 is loaded onto driving instrument 70. Driving instrument 70 is rotated to engage semi-rigid screw 14 or rigid screw 16 with bone. Driving instrument 70 is rotated until head 40 or head 44 contacts lead-in chamfer 36. Further rotating driving instrument 70 engages head 40 or head 44 to engage spherical concave undercut 32. Head 40 or head 44 is received and retained in spherical concave undercut 32. Additional semi-rigid screws 14 or rigid screws 16 are installed to complete the installation process of the fixation system 10.

It is contemplated that in one embodiment, ridges are included on the bone plate to reduce stress on the fastener receiving openings 18 and increase the fatigue life of the bone plate. Anterior surface 26 has stress-controlling ridges 90 situated further from the neutral axis of plate 12 than a recessed surface 92 with anterior surface 26 being relatively convex. It should be appreciated that one could use a single stress-controlling ridge as well as a plurality of the ridges depending on the deployment location of the ridges 90 on the plate. Furthermore, such stress-controlling ridges may be located on the posterior surface as well as the more typical anterior surface deployment.

It should be noted that posterior surface 28 is relatively concave and relatively smooth. It should be further appreciated that several forms of surface modifications are contemplated for posterior surface 28. Surface modifications contemplated include roughening the surface or making the surface porous to encourage bone ingrowth, as well as adding spikes, teeth, holes for bone ingrowth, or through holes for receiving wires, cables, nails, or sutures. Further contemplated surface modifications include treatments with bone-growth factors or other tissue-growth factors to enhance the healing process.

Turning to FIGS. 11–15, an embodiment of the present bone fixation system 100 is provided having a fusion cage 102 incorporated into bone plate 104. Fusion cages are used to promote fusion of the injured area and speed healing. In the present embodiment, this is accomplished by inserting, packing or impregnating bone graft tissue into a graft receiving area 106 of the fusion cage 102. After fixing the bone plate 104 to the vertebrae, the bone tissue graft will grow out through the openings or vascular windows 108 of the graft receiving area 106 to ultimately fuse with the healing vertebrae.

Specifically, the fusion cage embodiment 100 of the present invention generally comprises a fusion cage 102, bone plate 104, a graft receiving area 106 having a plurality of vascular windows 108 therethrough and fastener receiving openings 110, 112 for receiving bone screws or other such fasteners. The bone plate 104 of the fusion cage embodiment 100 has an anterior surface 114, a posterior surface 116, a caudal end 118 and a cephalad end 120. Fastener holes 110, 112 may have undercuts incorporated therein, and as described previously, are located through the bone plate 104. One of ordinary skill in the art, however, will readily appreciate that backout is greatly reduced, if not eliminated altogether, because loads placed on the device will transfer to and be borne by the graft receiving area 106 which is lodged between the vertebrae.

Cephalad fastener receiving openings 110 are angled so as the cephalad fasteners 122 are inserted through their respective holes 110 and into the bone to be treated, they are driven in the cephalad direction. The cephalad fasteners 122 are also preferably angled slightly toward an imaginary centerline of the bone plate 104, so that upon insertion, the cephalad fasteners 122 inserted into the cephalad fastener receiving openings 110 form a triangular wedge construct. If desired, the cephalad fastener receiving openings 110 and fasteners may utilize the snap-fit engagement of a head portion of the screw into an undercut located in the screw hole in a manner identical to that previously described.

The caudal fastener receiving openings 112 receive caudal fasteners or bone screws 124 which may "snap-fit" or engage respective undercuts in the caudal screw holes 112. Note, however, such snap-fit undercuts are not required, but if utilized are implemented as described above.

The graft receiving area 106 of the fusion cage 102 may have one or more vascular windows 108 incorporated therethrough. As illustrated, the vascular windows 108 have a circular configuration in which the outside edges are counter-sunk as a stress reducing feature. One of ordinary skill in the art would appreciate that the counter-sunk feature is non-critical and that the windows may have any number of configurations. Exemplary, but by no means limiting, configurations include ovals, hexagons, squares and even a single, large window.

The graft receiving area 106 of the fusion cage may also have endplate angles 126, 128 in both the cephalad and caudal directions. The angles 126, 128 are designed to rest against the vertebral endplate of a vertebra being treated. The angles 126, 128 may be included to maintain lordotic fit between the fusion cage 102 and the vertebral column. For illustration purposes only, FIG. 12, demonstrates that the angles are approximately 10°, but this angulation may change in either direction in order to improve the fit of the bone plate and may even be negative, depending upon the orientation of the vertebrae being treated. Finally, one of ordinary skill in the art would understand that the posterior surface 116 of the bone plate 104 may have a curvature designed to mirror the vertebral topology. Such use of contoured surfaces to mate with vertebral bodies is further described in U.S. patent application Ser. No. 09/114,996, incorporated by reference herein.

Having thus described the invention, it is now claimed:

1. A bone fixation apparatus comprising:
   a) a bone plate having a first end, a second end, a first edge extending from said first end to said second end, a second edge opposite said first edge and extending from said first end to said second end, a posterior surface for engaging a portion of the bone being fixated, an anterior surface, and at least one fastener receiving opening therethrough, said at least one fastener receiving opening including at least one undercut wherein said anterior surface of said bone plate has at least one stress controlling ridge substantially positioned in the longitudinal direction and not coincident with the neutral axis, and
   b) at least one fastener having a head portion, said fastener being received and retained by said at least one fastener receiving opening with said head portion engaging said at least one undercut.

2. A bone fixture apparatus comprising:
   a) a bone plate having a first end, a second end, a first edge extending from said first end to said second end, a second edge opposite said first edge and extending from said first end to said second end, a posterior surface for engaging a portion of the bone being fixated, an anterior surface, and at least one fastener receiving opening therethrough, said at least one fastener receiving opening including at least one undercut wherein said posterior surface of said bone plate has at least one stress controlling ridge substantially positioned in the longitudinal direction and not coincident with the neutral axis, and
   b) at least one fastener having a head portion, said fastener being received and retained by said at least one fastener receiving opening with said head portion engaging said at least one undercut.

3. A bone fixation apparatus comprising:
   a) a bone plate having a first end, a second end, a first edge extending from said first end to said second end, a second edge opposite said first edge and extending from said first end to said second end, a posterior surface for engaging a portion of the bone being fixated, an anterior surface, and at least one fastener receiving opening therethrough, said at least one fastener receiving opening having a protrusion section wherein said anterior surface of said bone plate has at least one stress controlling ridge positioned in the longitudinal direction and not coincident with the neutral axis; and
   b) at least one fastener having a head portion, said head portion capable of mating with said protrusion of said fastener receiving opening.

4. A bone fixation apparatus comprising:
   a) a bone plate having a first end, a second end, a first edge extending from said first end to said second end, a second edge opposite said first edge and extending from said first end to said second end, a posterior surface for engaging a portion of the bone being fixated, an anterior surface, and at least one fastener receiving opening therethrough, said at least one fastener receiving opening having a protrusion section wherein said posterior surface of said bone plate has at least one stress controlling ridge positioned in the longitudinal direction and not coincident with the neutral axis; and
   b) at least one fastener having a head portion, said head portion capable of mating with said protrusion of said fastener receiving opening.

5. A bone fixation apparatus comprising:
   a) a bone plate having a first end, a second end, a first edge extending from said first end to said second end, a second edge opposite said first edge and extending from said first end to said second end, a posterior surface for engaging a portion of the bone being fixated, an anterior surface, and a plurality of fastener receiving openings therethrough, said plurality of fastener receiving openings including an undercut therein wherein said anterior surface of said bone plate has at least one stress controlling ridge positioning in the longitudinal direction and not coincident with the neutral axis; and
   b) a plurality of fasteners having a head portion, said plurality of fasteners being received and retained by said plurality of fastener receiving openings with said head portion engaging said undercut.

6. A bone fixation apparatus comprising:
   a) a bone plate having a first end, a second end, a first edge extending from said first end to said second end, a second edge opposite said first edge and extending from said first end to said second end, a posterior surface for engaging a portion of the bone being fixated, an anterior surface, and a plurality of fastener receiving openings therethrough, said plurality of fastener receiving openings including an undercut therein wherein said posterior surface of said bone plate has at least one stress controlling ridge positioning in the longitudinal direction and not coincident with the neutral axis; and
   b) a plurality of fasteners having a head portion, said plurality of fasteners being received and retained by said plurality of fastener receiving openings with said head portion engaging said undercut.

7. A bone fixation fusion cage apparatus comprising:
   a.) a bone plate having a caudal end, a cephalad end, a posterior surface for engaging a bone to be fixated, an anterior surface, a plurality of fastener receiving openings therethrough;
   b.) a plurality of fasteners capable of insertion into said plurality of fastener receiving openings; and
   c.) a graft receiving area connected to said bone plate; said graft receiving area having at least one vascular window therethrough wherein said graft receiving area further comprises a cephalad end plate angle.

8. The bone fixation fusion cage apparatus of claim 7 wherein said plurality of fastener receiving openings includes at least one caudal fastener receiving opening.

9. The bone fixation fusion cage apparatus of claim 7 wherein said plurality of fasteners includes at least one caudal fastener.

10. The bone fixation fusion cage apparatus of claim 9 wherein said at least one caudal fastener further comprises a head portion.

11. The bone fixation cage apparatus of claim 10 wherein said at least one caudal fastener receiving opening further comprises an undercut portion therein for engaging said head portion of said at least one caudal fastener.

12. The bone fixation fusion cage apparatus of claim 7 wherein said plurality of fastener receiving openings includes at least one cephalad fastener receiving opening.

13. The bone fixation fusion cage apparatus of claim 7 wherein said plurality of fasteners includes at least one cephalad fastener.

14. The bone fixation fusion cage apparatus of claim 13 wherein said at least one cephalad fastener further comprises a head portion.

15. The bone fixation cage of claim 14 wherein said at least one cephalad fastener receiving opening further comprises an undercut portion therein for engaging said head portion of said at least one cephalad fastener.

16. A bone fixation fusion cage apparatus comprising:
   a.) a bone plate having a caudal end, a cephalad end, a posterior surface for engaging a bone to be fixated, an anterior surface, a plurality of fastener receiving openings therethrough;
   b.) a plurality of fasteners capable of insertion into said plurality of fastener receiving openings; and
   c.) a graft receiving area connected to said bone plate; said graft receiving area having at least one vascular window therethrough wherein said graft receiving area further comprises a caudal end plate angle.

17. The bone fixation fusion cage apparatus of claim 16 wherein said plurality of fastener receiver openings includes at least one caudal fastener receiver opening.

18. The bone fixation fusion cage apparatus of claim 16 wherein said plurality of fasteners includes at least one caudal fastener.

19. The bone fixation fusion cage apparatus of claim 18 wherein said at least one caudal fastener further comprises a head portion.

20. The bone fixation cage apparatus of claim 19 wherein said at least one caudal fastener receiving opening further comprises an undercut portion therein for engaging said head portion of said at least one caudal fastener.

21. The bone fixation fusion cage apparatus of claim 16 wherein said plurality of fastener receiving openings includes at least one cephalad fastener receiving opening.

22. The bone fixation fusion cage apparatus of claim 16 wherein said plurality of fasteners includes at least one cephalad fastener.

23. The bone fixation fusion cage apparatus of claim 22 wherein said at least one cephalad fastener further comprises a head portion.

24. The bone fixation cage of claim 23 wherein said at least one cephalad fastener receiving opening further comprises an undercut portion therein for engaging said head portion of said at least one cephalad fastener.

* * * * *